US008603282B2

(12) United States Patent
Del Sarto

(10) Patent No.: US 8,603,282 B2
(45) Date of Patent: Dec. 10, 2013

(54) ADHESIVE ELEMENT FOR ADHESION TESTS AND CORRESPONDING TESTING PROCESS

(75) Inventor: Chiara Del Sarto, Turin (IT)

(73) Assignee: Jenyo S.r.l. Unipersonale, Turin (IT)

( * ) Notice: Subject to any disclaimer, the term of this patent is extended or adjusted under 35 U.S.C. 154(b) by 0 days.

(21) Appl. No.: 13/259,693

(22) PCT Filed: Mar. 29, 2010

(86) PCT No.: PCT/IB2010/051352
§ 371 (c)(1),
(2), (4) Date: Dec. 9, 2011

(87) PCT Pub. No.: WO2010/119361
PCT Pub. Date: Oct. 21, 2010

(65) Prior Publication Data
US 2012/0090762 A1    Apr. 19, 2012

(30) Foreign Application Priority Data
Apr. 14, 2009  (IT) .............................. TO2009A0287

(51) Int. Cl.
*B32B 38/10*    (2006.01)
(52) U.S. Cl.
USPC .............................. 156/247; 156/64; 156/378
(58) Field of Classification Search
USPC .............................. 156/64, 247, 378; 425/354
See application file for complete search history.

(56) References Cited

U.S. PATENT DOCUMENTS

| 5,725,960 A | 3/1998 | Konishi et al. |
| 6,309,745 B1 | 10/2001 | Willms et al. |
| 2004/0020592 A1 | 2/2004 | Dietz et al. |
| 2008/0156444 A1 | 7/2008 | Pitzen et al. |

FOREIGN PATENT DOCUMENTS

| DE | 102004062325 A1 | 6/2006 | |
| JP | 06-034520 | * 2/1994 | ............. G01N 19/04 |
| JP | 06034520 A | 2/1994 | |

OTHER PUBLICATIONS

International search report for application No. PCT/IB2010/051352 dated Jun. 2, 2010.
European Office Action dated Apr. 5, 2013, EPO Application No. 10713002.3.

* cited by examiner

*Primary Examiner* — Yogendra Gupta
*Assistant Examiner* — Vishal I Patel

(57) ABSTRACT

An adhesive element for adhesion tests, comprising a bi-adhesive layer including a first adhesive surface, designed to co-operate in a relation of adhesion with a surface undergoing testing, and a second adhesive surface. The adhesive element further comprises a support layer having a comparative adhesion surface designed to co-operate in a relation of adhesion with the second adhesive surface. The bi-adhesive layer has a fragmented structure.

5 Claims, 6 Drawing Sheets

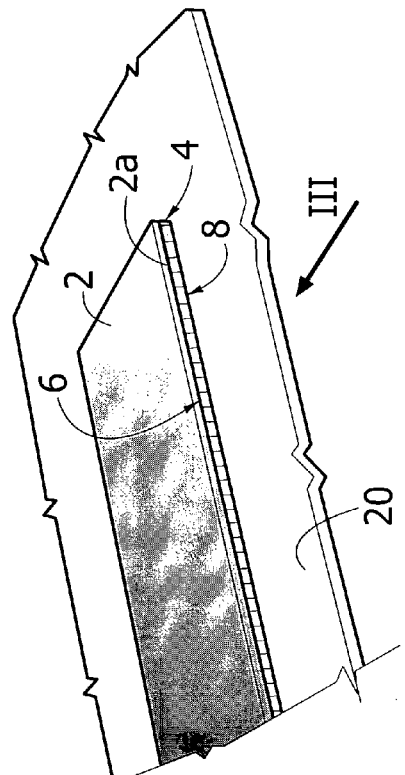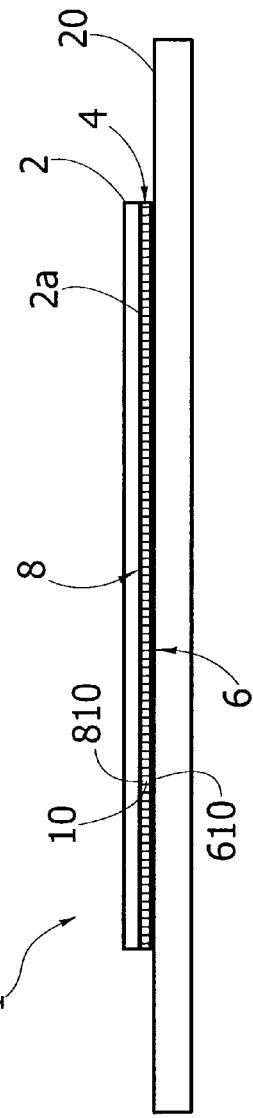

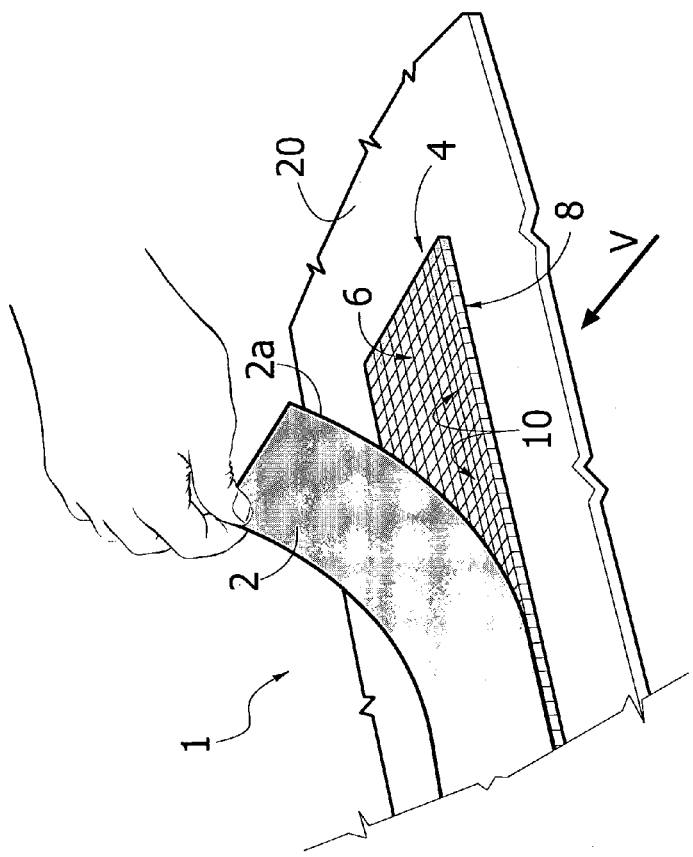
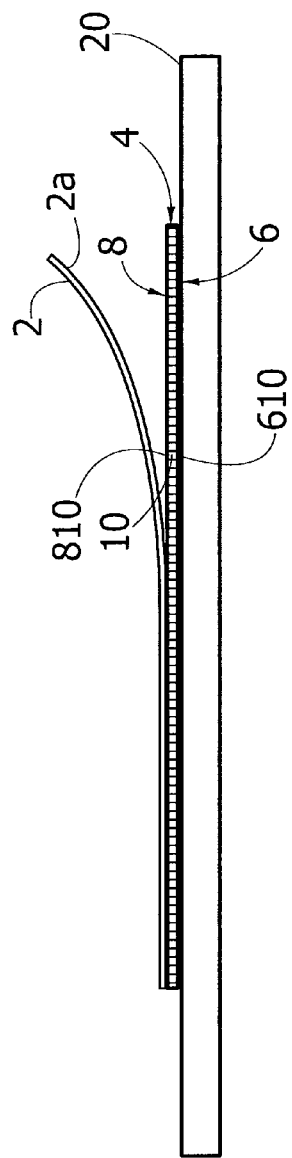
FIG. 4
FIG. 5

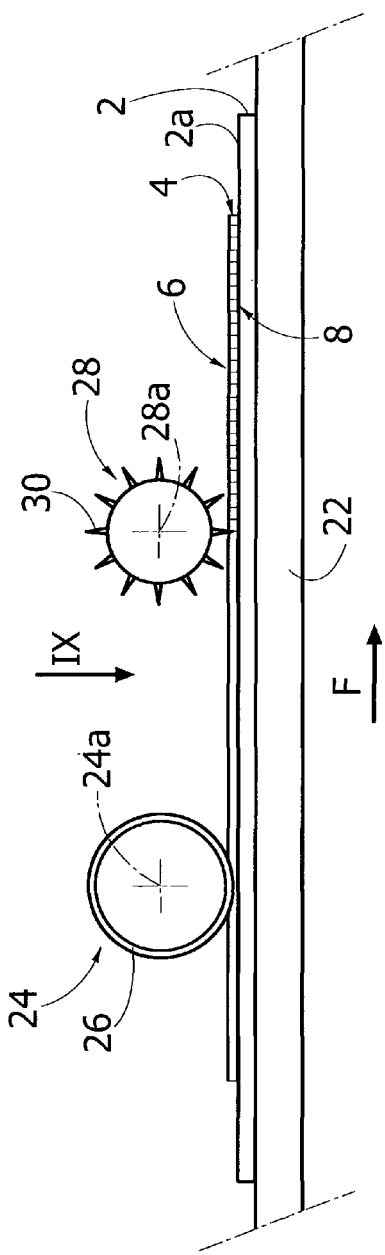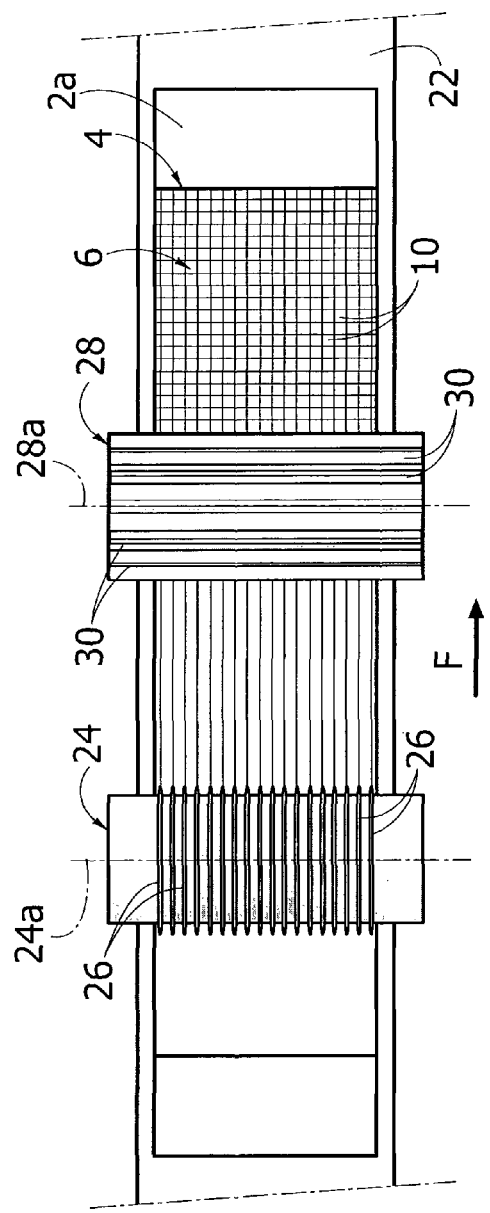

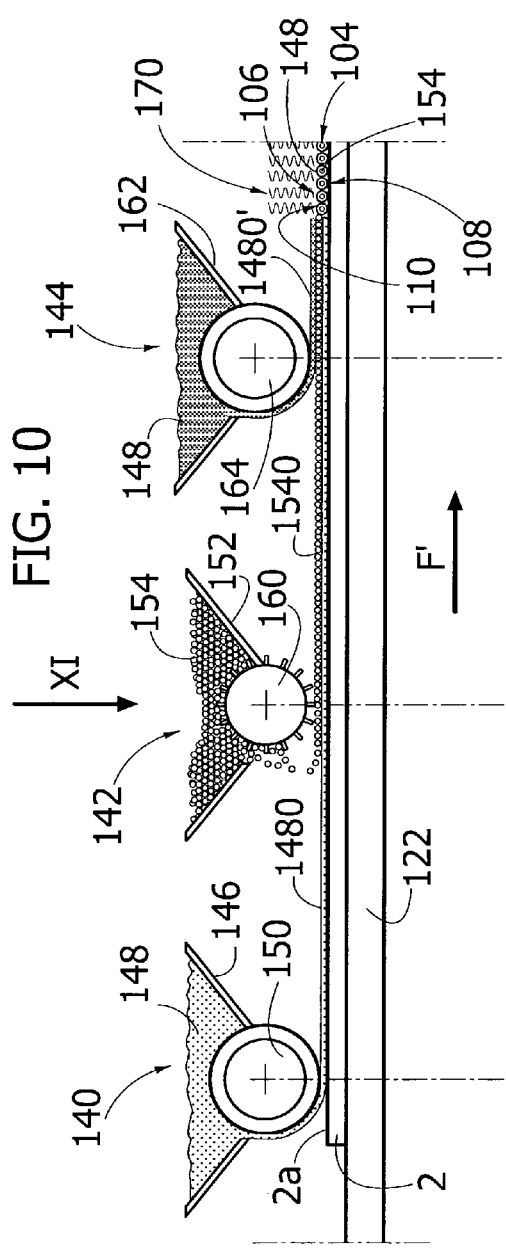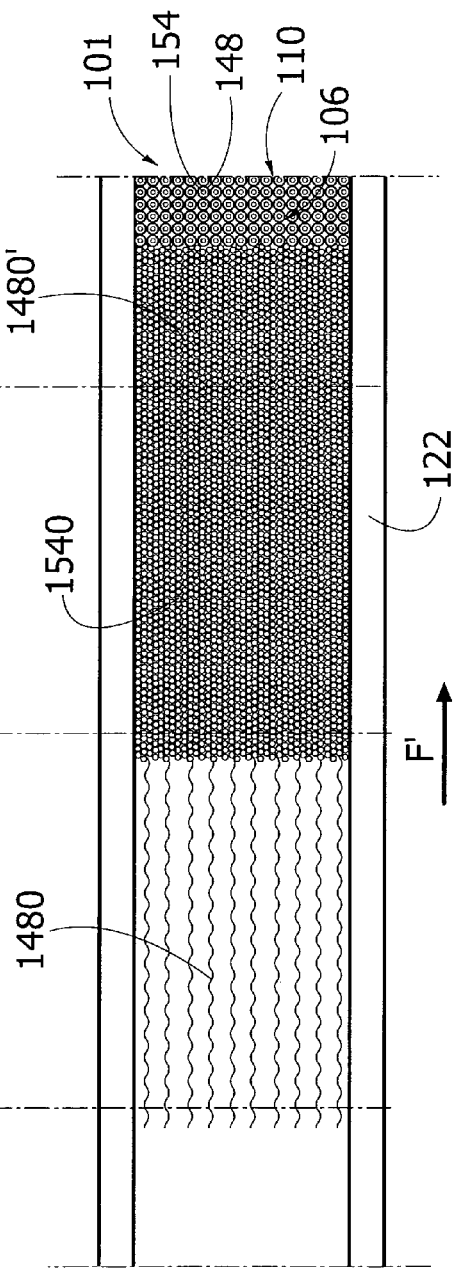

ADHESIVE ELEMENT FOR ADHESION TESTS AND CORRESPONDING TESTING PROCESS

FIELD OF THE INVENTION

The present invention relates to an element and a process for subjecting surfaces that may undergo coating treatments to adhesion tests. In particular, the invention regards an adhesive element, particularly in the form of a strip, adhesion tests on surfaces of various types, and a corresponding testing process.

DESCRIPTION OF THE PRIOR ART

In industrial practice, there is frequently the need to apply a treatment of surface coating to different objects or surfaces. Said need derives, for example, from requirements of decoration, protection, or attachment.

Whatever the coating treatment applied, a surface that is to undergo the treatment must present characteristics such as to promote and maintain the bond with the coating. This is of fundamental importance for the purpose of guaranteeing a high quality of the product treated, whether it is a raw material, a semifinished product, or a finished product.

There exist in this regard standards for the measurement or verification of the properties of adhesion of a surface on which a coating is applied, and, in general, the known art envisages execution of the measurement or verification with different products and methods.

A first method consists in the measurement of the angle of contact between a drop of a test liquid and a surface subjected to measurement.

It is necessary to take a test specimen, comprising the surface subjected to measurement, which is subsequently positioned on a support associated to a lamp. The lamp is set for projecting the profile of the specimen on a screen having a graduated scale.

The measurement process envisages deposition on the surface of a drop of the aforesaid test liquid, droplets of generally distilled water calibrated and treated by means of a micronizer, of which the tangent of the angle of contact with respect to the surface itself is measured. The measurement is performed thanks to the projection of the profile of the specimen and of the drop on the aforesaid screen by means of the lamp. The higher the value measured of the tangent of the angle of contact, the lower the degree of adhesion of the surface.

The process is hence very precise and provides an absolute indication, but is applicable only in the laboratory by means of dedicated and very costly equipment. In addition, generally, the process is of a destructive type since it envisages taking of a sample.

Given moreover the mode of measurement, it is evident that it is not possible to make the measurement in this way on porous materials, in which the test liquid would be rapidly absorbed.

A second solution used in the framework of the known art envisages the use of a test ink and enables a measurement of a comparative, i.e., non-absolute, nature to be obtained. Briefly, each test ink is associated to a given value of wettability of a surface.

The test envisages spreading the test ink over the surface to be tested, for example using a paintbrush, and yields a positive result in the case where the ink is distributed in a uniform way, for example, to form a film on the surface. This means that the surface has a value of wettability higher than the value to which the ink is associated, but the absolute value of wettability is not known.

However, the method is not particularly precise and calls for considerable experience in the interpretation of the results.

In addition, the different volatility of the components of the test ink can easily lead to alterations in the results.

Finally, it is to be noted that the wettability of a surface is in general a condition necessary for a good adhesion thereof, but is not in any case a sufficient condition.

To assess the characteristics of adhesion of a surface the known art envisages use of processes, in general comparative tests, based upon application and subsequent removal of an adhesive tape by means of a dynamometric arm. In general, these tests can be conducted, alternatively, before or after application of the coating treatment.

In the case where the test is executed before the coating treatment a strip of adhesive material is set on the surface, and the force required for its detachment is measured. However, this method provides average information of the characteristics of adhesion of the surface in so far as with a single tape it is impossible to obtain precise information. Above all, this implies that the low forces that develop in points at low degrees of adhesion, which is an indication of extremely poor characteristics of the surface, can be easily masked by forces of greater magnitude that develop in points with high degree of adhesion, hence thus rendering the test far from reliable.

If, instead, the test is conducted after application of the coating, a strip of adhesive tape is applied on a portion of coating in which an incision has previously been made, for example, according to a quadrangular-mesh geometry, and then the adhesive is removed.

In the case where the test is successful the coating is not removed. However, the process is evidently of a destructive type for the coating.

OBJECT OF THE INVENTION

The object of the present invention is to overcome the problems of the prior art. In particular, the object of the invention is to provide a product for conducting an adhesion test on any surface and a corresponding testing process presenting a lower cost, sufficient precision, ease of interpretation, and a non-destructive nature.

SUMMARY OF THE INVENTION

The object of the invention is achieved by an adhesive element, particularly in the form of a strip, for adhesion tests and a process having the characteristics forming the subject of the ensuing claims, which constitute an integral part of the technical teaching provided herein in relation to the invention.

In particular, this object is achieved by an adhesive element comprising a bi-adhesive layer with fragmented structure and by a corresponding testing process.

BRIEF DESCRIPTION OF THE DRAWINGS

The invention will now be described in detail with reference to the attached drawings, which are provided purely by way of non-limiting example and in which:

FIG. 1 is a perspective view of an adhesive element according to a first embodiment of the present invention;

FIGS. 2, 4, and 6 are perspective views illustrating steps of a testing process according to the invention;

FIGS. 3, 5, and 7 are side views according to the arrows III, V, and VII of FIGS. 2, 4, and 6, respectively;

FIG. 8 is a schematic side view of a part of a line for production of the first embodiment of the adhesive element according to the invention;

FIG. 9 is a plan view according to the arrow IX of FIG. 8;

FIG. 10 is a schematic side view of a part of a line for production of an adhesive element according to a second embodiment of the invention;

FIG. 11 is a plan view according to the arrow XI of FIG. 10; and

DETAILED DESCRIPTION OF THE INVENTION

Figure 6:
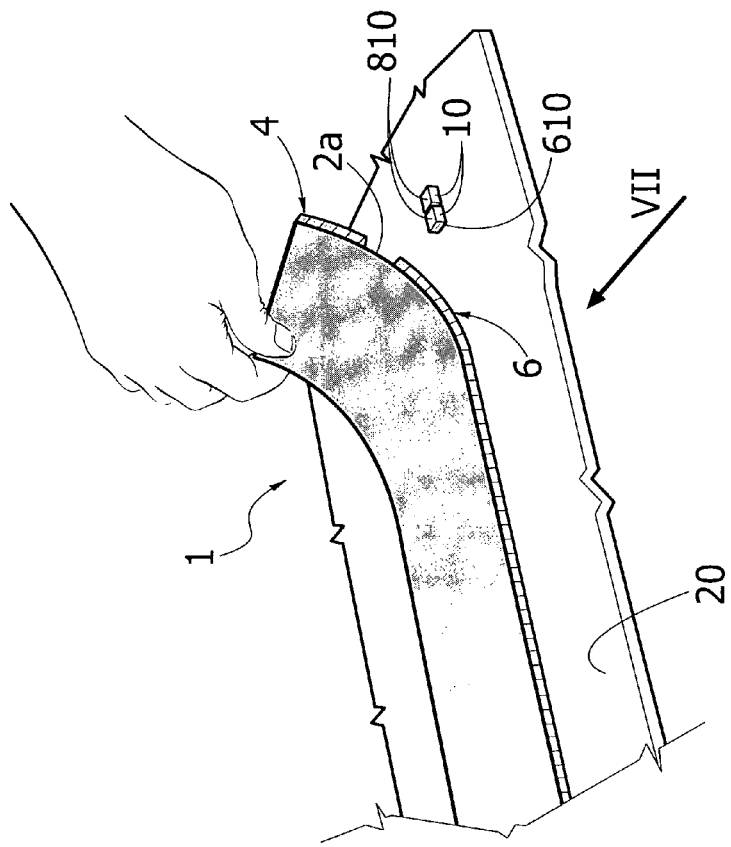

In FIG. 1 designated by 1 is a first embodiment of an adhesive element, particularly in the form of a strip, according to the present invention. It will be appreciated that the adhesive element can have any shape according to the requirements of application. The adhesive element 1 comprises a support layer 2 and a bi-adhesive layer 4. The support layer 2 has, in a preferred variant, a fabric structure, but clearly other solutions are possible.

The bi-adhesive layer 4 is a flexible layer having a pair of opposed surfaces coated with a dried adhesive. In particular, the bi-adhesive layer 4 comprises a first adhesive surface 6 and a second adhesive surface 8.

The bi-adhesive layer 4 has a fragmented structure, which, in this embodiment, comprises a plurality of quadrangular pieces 10. Each quadrangular piece 10, defining a fragment of the bi-adhesive layer 4, has a face 610 forming part of the first adhesive surface 6 and a face 810 forming part of the second adhesive surface 8. In a preferred variant, the pieces 10 are square in shape.

The bi-adhesive layer 4 is applied on the support layer 2, particularly on a comparative adhesion surface 2a, designed to co-operate in a relation of adhesion with the second adhesive surface 8 of the bi-adhesive layer 4.

The support layer 2 is obtained with different materials according to the degree of adhesion that it is intended to assign to the comparative adhesion surface 2a, as will be described in detail hereinafter.

Illustrated in FIGS. 2 to 7 are steps of a testing process for evaluating an index of adhesion of a surface 20 by using the adhesive element 1.

With reference to FIGS. 2 and 3, the testing process comprises a first step of application of the adhesive element 1 on a surface 20 undergoing testing. The adhesive element 1 is applied so as to cause adhesion thereof with the surface 20. In particular, adhesion is caused between the first adhesive surface 6 and the surface 20.

Hence, the first adhesive surface 6 is designed to co-operate in a relation of adhesion with the surface 20 undergoing testing.

With reference to FIGS. 4 to 7, the process comprises, following upon the first step, a second step of removal of the support layer 2 from the bi-adhesive layer 4 executed manually or with automatic means (not illustrated), and a third step of evaluation of the distribution of the fragments of the bi-adhesive layer 4. This means that, following upon removal of the support layer 2 from the bi-adhesive layer 4, there occurs the presence of fragments on the comparative adhesion surface 2a or, according to the requirements, on the surface 20, as will be described in detail hereinafter.

It is evident that the quadrangular piece 10 defines, in this embodiment, the aforesaid fragments of the bi-adhesive layer 4.

In detail, the comparative adhesion surface 2a of the support layer 2 imposes a reference value for evaluation of the degree of adhesion of the surface 20 undergoing testing. In fact, the bi-adhesive layer 4 is applied both on the surface 20 by means of the first adhesive surface 6 and on the comparative adhesion surface 2a of the support layer 2 by means of the second adhesive surface 8.

Since the aforesaid surfaces 6 and 8 of the bi-adhesive layer 4 are coated with one and the same adhesive, the development, at the interface between the second adhesive surface 8 and the comparative adhesion surface 2a, of forces of adhesion that have a modulus different from that of the forces of adhesion that arise at the interface between the first adhesive surface 6 and the surface 20 depends only upon the characteristics of adhesion of the surfaces 2a, 20.

In particular, the force acting on the face 610 of each quadrangular piece 10 is determined by the degree of adhesion of the surface 20 with respect to the first adhesive surface 6 of the bi-adhesive layer 4, whereas the force acting on the face 810 of each quadrangular piece 10 is fixed and is given by the degree of adhesion of the comparative adhesion surface 2a with respect to the bi-adhesive layer 4, chosen during production of the adhesive element 1.

This implies that, at the moment of removal of the support layer 2 from the bi-adhesive layer 4, each quadrangular piece 10 comes to be subjected to the action of two antagonistic forces acting, respectively, on the face 610 and on the face 810.

In this way, with reference to FIGS. 4 and 5, if the surface 20 everywhere has a degree of adhesion greater than that of the comparative adhesion surface 2a, the entire quadrangular piece 10 remains attached to the surface 20. In this case, the test yields a positive result.

This occurs evidently because the forces of adhesion developed at the interface between the surface and the first adhesive surface 6 are higher than those that develop at the interface between the second adhesive surface 8 and the comparative adhesion surface 2a; hence, the force acting on each face 610 has a magnitude greater than that acting on the face 810.

Figure 7:
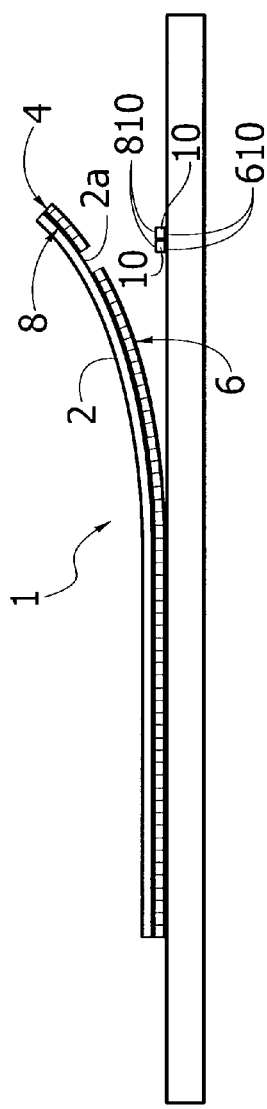

Instead, as illustrated in FIGS. 6 and 7, if the surface 20 locally has a degree of adhesion lower than that of the comparative adhesion surface 2a of the support layer 2, part of the quadrangular pieces 10 remains attached to the comparative adhesion surface 2a.

Clearly, in the case where the degree of adhesion of the surface 20 is lower than that of the comparative adhesion surface 2a throughout the area of the adhesive element 1, the totality of the quadrangular pieces 10 remains attached to the comparative adhesion surface. In either case, the result of the test is negative. In general, even in the presence of a single quadrangular piece 10 attached to the comparative adhesion surface 2a following upon removal of the support layer 2, the result of the test is to be considered negative.

In fact, in the cases mentioned above, the force of adhesion acting on the face 610 of each quadrangular piece 10 is lower than the force acting on the face 810 in the points where the surface 20 has a degree of adhesion lower than that of the comparative adhesion surface 2a.

In this way, the role of the support layer 2 and in particular of the comparative adhesion surface 2a is clear: the material of which the support layer 2, and hence also the surface 2a, is made imposes a reference for assessing the degree of adhesion of the surface 20.

However, it is evident that according to the material of which the surface 20 is made and the type of coating that it is intended to apply thereto the reference value for the index of adhesion associated to the comparative adhesion surface 2a must be varied. This can be obtained by making the support layer 2, in particular the comparative adhesion surface 2a, of different materials having a different degree of adhesion in regard to the adhesive that coats the bi-adhesive layer 4.

Examples of materials that can be used to obtain the support layer 2, corresponding to as many reference values of the degree of adhesion established by international standards, are polyvinyl chloride (PVC), polycarbonate (PC), or Teflon (PTFE).

It is hence clear that the adhesive element 1 and the testing process described above enable adhesion tests to be carried out on a surface in a fast and precise way and on the basis of a comparison between a reference degree of adhesion, which is known, and a value detected locally. In addition, since it is not a measurement of wettability, such as, for example, the measurements of the angle of contact or the measurements with ink, it is an expression of the real properties of adhesion of a surface and can be used also on porous materials.

It is moreover possible to modulate the resolution of the test by varying the dimensions of the quadrangular pieces 10. The smaller the dimensions of the pieces 10, the greater the possibility of detecting defects of small extension, which otherwise would be masked in a way similar to what occurs in tests carried out with non-fragmented tapes. Likewise, it is in this way possible to conduct tests also on items of small size, which would otherwise be impossible or in any case very complex to carry out.

Furthermore, it will be appreciated that the testing process is of a non-destructive type and does moreover not require particular experience in reading the results. The result of a test executed by means of the adhesive element 1 and the testing process described above can be interpreted on the basis of a simple binary logic associated to a visual finding, i.e., to the evaluation of the distribution of the fragments of the bi-adhesive layer 4.

As regards the aspect of the reduction of the costs of the adhesion tests, it should be noted that for the production of an adhesive element 1 according to the invention, it is possible to combine to the traditional process of production of bi-adhesive tapes, which is in itself known and hence not described in detail, an additional treatment that envisages a double rotary cutter, as illustrated in FIGS. 8 and 9, which illustrate a part of a line for production of the adhesive element 1.

In particular, it is possible to provide a surface of horizontal sliding 22 on which, in a longitudinal direction designated by F in FIG. 8, a support layer 2 advances. On the support layer 2 there has already been applied, on the opposite side with respect to the surface of sliding 30, a bi-adhesive layer 4.

During advance of the support layer 2 and of the bi-adhesive layer 4, applied thereon and fixed thereto, the bi-adhesive layer 4 encounters, in sequence, a first cutting tool 24, rotating about a horizontal transverse axis 24a and having a plurality of longitudinal annular blades 26, and a second cutting tool 28, which in turn rotates about a horizontal transverse axis 28a and has a plurality of transverse rectilinear blades 30.

In a way in itself known, the combined action of the first cutting tool 24 and of the second cutting tool 28 creates the quadrangular pieces 10 in the bi-adhesive layer 4, without making incisions in the support layer 2.

Hence, using processes and tools in themselves known it is possible to produce the adhesive element 1 with sufficiently contained production costs so as to be able to propose on the market the adhesive element 1 at a price decidedly lower that that of other products.

FIGS. 10 and 11 illustrate an adhesive element 101, particularly in the form of a strip according to a second embodiment of the invention, together with a part of a production line.

In a way similar to what has been said for the adhesive element 1, is will be appreciated that the embodiment mentioned above may be varied according to the requirements and the applications and in no way constitutes a limitation for the purposes of the invention.

The adhesive element 101 comprises the support layer 2 having the comparative adhesion surface 2a, applied on which is a bi-adhesive layer 104 with fragmented structure having a first adhesive surface 106 and a second adhesive surface 108.

The bi-adhesive layer 104 comprises, in this embodiment, a plurality of adhesive spheres 110 that define fragments of the bi-adhesive layer 4 and provide, in a way substantially similar to the case of the element 1, the aforesaid first and second adhesive surfaces 106 and 108. In a way similar to what has been described for the adhesive element 1, the comparative adhesion surface 2a is designed to co-operate in a relation of adhesion with the second adhesive surface 108, whereas the first adhesive surface 106 is designed to co-operate in a relation of adhesion with a surface undergoing testing.

It is evident that the adhesive spheres 110 have the same function as the quadrangular pieces 10 of the adhesive element 1. Also the steps of the testing process and the mode of interpretation of the results remain identical and consequently will not be described again.

The only difference lies in the fact that the faces 610 and 810 of the quadrangular pieces 10 are here replaced by areas of contact, respectively, between each sphere 110 and the surface 20, and each sphere 110 and the comparative adhesion surface 2a. Hence, the surfaces 106, 108 are substantially defined by a plurality of adjacent areas of contact afforded by the adhesive spheres 110.

The part of production line illustrated in FIGS. 10 and 11 is provided for implementing a production process, which comprises the use of a surface of sliding 122 on which the support layer 2 with the comparative adhesion surface 2a facing upwards advances in a longitudinal direction designated by F'.

During advance of the support layer 2 in the longitudinal direction F', the comparative adhesion surface 2a encounters, in sequence, a first dispenser of adhesive 140, a dispenser of spheres 142, and a second dispenser of adhesive 144.

The first dispenser of adhesive 140 comprises a hopper 146, within which an adhesive 148 is housed, which is deposited on the comparative adhesion surface 2a by a dispensing roller 150 turning about a first horizontal transverse axis 150a.

The adhesive 148 thus deposited forms a first layer 1480 of adhesive on the comparative adhesion surface 2a.

The dispenser of spheres 142 comprises a hopper 152, housed within which is a plurality of spheres 154, which are deposited on the first layer 1480 of adhesive by a paddle roller 160, which turns about a second horizontal transverse axis 160a. The spheres 26' that come to rest on the layer 1480 form in turn a layer 1540 of spheres.

Finally, the second bi-adhesive dispenser 144 comprises a hopper 162, housed inside which is the adhesive 148, which is deposited on the layer 1540 of spheres by a dispensing roller 164 that turns about a third horizontal transverse axis 164*a*. In this way, a second layer 1480' of adhesive is formed above the layer 1540 of spheres.

Next, for example by means of drying with infrared radiation, a process in itself known and represented schematically with wavy lines 170, there is brought about coagulation of the layers 1480 and 1480' around the spheres 154 of the layer 1540, thus obtaining a bi-adhesive layer 4 comprising adhesive spheres 110. Each adhesive sphere 110 comprises a sphere 154 coated with adhesive 148.

The spheres 154 can be conveniently made of metal material, typically aluminium. It may, however, be noted that this in no way limits the scope of the invention: the choice can fall on other materials, including non-metal materials, without thereby departing from the idea underlying the invention.

Figure 12:
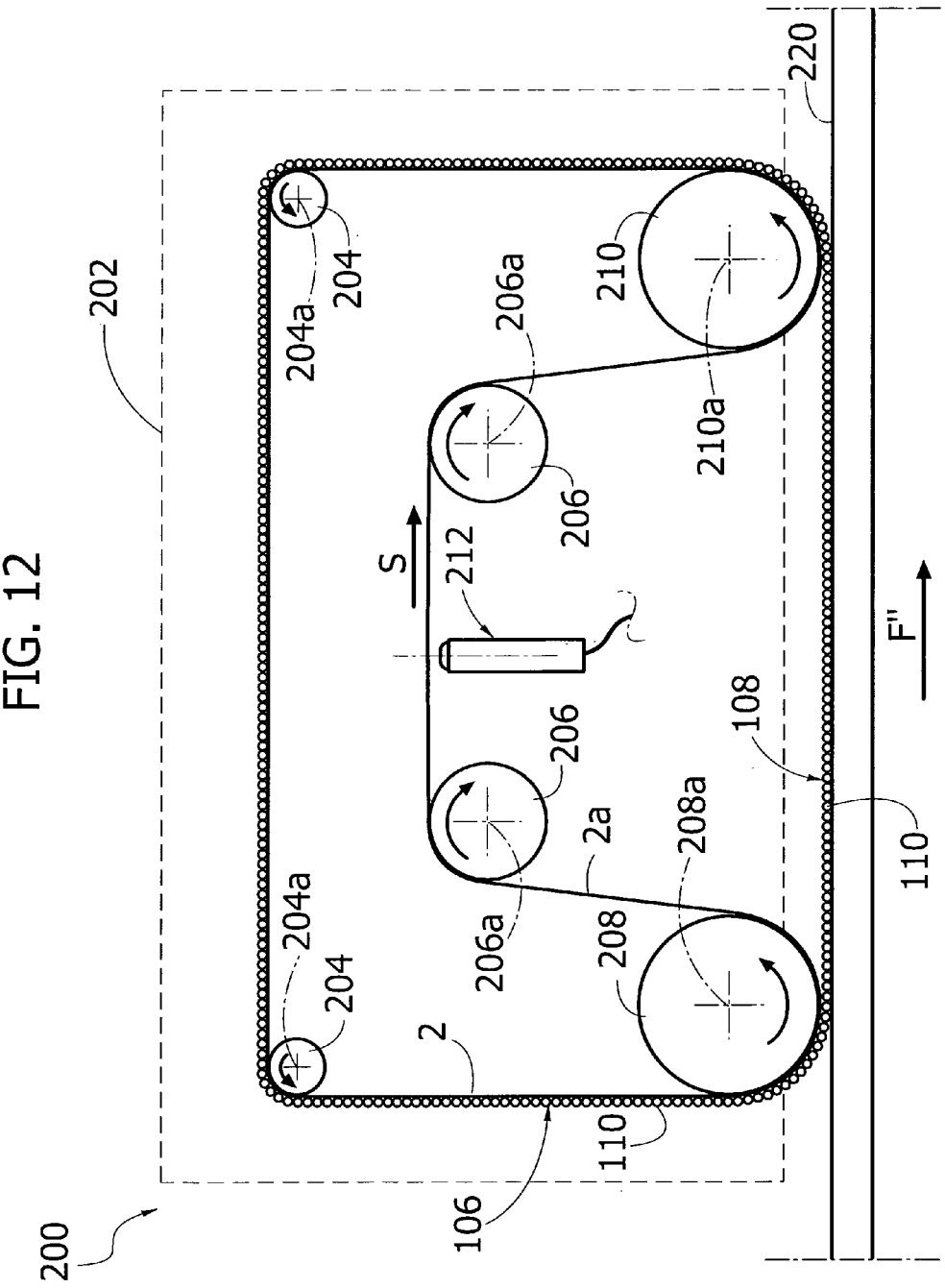
FIG. 12 is a schematic side view of a testing machine that uses the adhesive element of FIGS. 10 and 11.

If the spheres 154 are made of ferromagnetic metal material, it is possible to automate the process for testing the characteristics of adhesion, adapting it to tests to be conducted on continuous process lines, such as for example a line for painting sheet metal, by using an automatic testing machine 200, schematically illustrated in FIG. 12.

The automatic testing machine 200 comprises, in a casing 202, three pairs of rollers set symmetrically with respect to a vertical axis. The rollers are substantially arranged to form an "H".

In particular, the machine 200 comprises a first pair of rollers 204, rotating about respective parallel and horizontal axes 204*a*, a second pair of rollers 206, rotating about respective parallel and horizontal axes 206*a*, and a third pair of rollers 208, 210, rotating about respective parallel and horizontal axes 208*a* and 210*a*. The rollers 206 are set underneath the rollers 204, and the rollers 208 and 210 are in turn set underneath the rollers 206. The roller 210 is magnetic.

The rollers 204 have in general a diameter smaller that that of the rollers 206, which in turn have a diameter smaller than that of the rollers 208, 210.

Wound on the three pairs of rollers is an adhesive element 101.

The adhesive element 101 defines a closed path, having substantially the shape of a "U" turned upside down, containing the rollers 204, 208 and 210, in which the adhesive spheres 110 face the outside of the closed path itself. Hence, the first adhesive surface 106 faces the outside of the closed path defined by the adhesive element 101.

The rollers 206 are positioned externally with respect to the closed path defined by the adhesive element 101, and set between them is a sensor 212, with vertical axis, for example of the induction type.

Hence, the lateral surface of the rollers 204, 208, 210 is in contact with a surface of the support layer 2 opposite to the comparative adhesion surface 2*a*, whereas the lateral surface of the rollers 206 is in contact, in general, with the comparative adhesion surface 2*a*.

Underneath the rollers 208 and 210, in contact with portions of adhesive element 101 wound thereon, a surface 220 that is to undergo adhesion testing advances horizontally in a direction designated by F".

Operation of the machine 200 is described in what follows.

One of the rollers, for example the roller 208, is coupled to an electric motor, and the remaining rollers are driven in rotation thanks to the fact that the adhesive element 101, which proceeds in a direction S, is wound on them. All the rollers have axes oriented in a transverse direction with respect to the direction S. It may be noted that, as will emerge clearly hereinafter, the machine 200 operates in a unidirectional way: the single direction of advance admissible for the adhesive element 101, without prejudice to the arrangement and the characteristics of the rollers described previously, is the direction S.

Simultaneously, with means in themselves known, advance of the surface 220 is imposed, at a speed equal to the peripheral velocity of the adhesive element wound on the rollers 208, 210.

The roller 208 is able to bring about adhesion of the spheres 110 on the surface 220 via the contact between the first adhesive surface 106 of a portion of adhesive element 101 wound thereon and the surface 220 itself.

At the same time, the roller 208 is able to remove the support layer 2 thanks to the orientation of the closed path defined between the roller 208 itself and the roller 206 immediately close thereto. In fact, between the roller 208 and the roller 206 immediately close thereto the adhesive element 101, particularly the support layer 2, is deviated at almost right angles with respect to the surface 220, in this way reproducing a typical movement of an action of removal.

The conditions whereby adhesion of the spheres 110 to the surface 2*a* of the support layer 2 or to the surface 220 is obtained are identical to the ones described previously and hence will not be described in any further detail.

In the event where at least one adhesive sphere 110 remains attached to the comparative adhesion surface 2*a*, with modalities similar to what has been described previously, its presence can be detected by the sensor 212, which in turn can communicate to an external control unit (not illustrated), the presence of a surface portion that is not compliant with the degree of adhesion required for application of the coating treatment, whatever this may be.

After passing beyond the sensor 212, the adhesive element 101, in particular the support layer 2 alone, proceeds towards the roller 210. The roller 210 is magnetic and is calibrated for developing a force of magnetic attraction on the spheres that is markedly greater than a maximum force of adhesion that can be developed between the adhesive spheres 110 and the surface 220. In this way, it is possible to bring the adhesive spheres 110 back onto the comparative adhesion surface 2*a* of the support layer 2, and the testing process can thus proceed in a continuous way.

Of course, without prejudice to the principle of the invention, the details of construction and the embodiments may vary widely with respect to what has been described and illustrated purely by way of example herein, without thereby departing from the scope of the present invention.

For example, the comparative adhesion surface 2*a* of the support layer 2 can be pre-arranged for application of a surface painting having a reference index of adhesion. In this way, it is possible to vary the reference value to be adopted in the tests by simply changing the type of paint used for coating the comparative adhesion surface 2*a*.

It is moreover possible to conduct tests in sequence using a silicone support layer, which can be easily detached. In this way, following upon the steps of application of the adhesive element 1, 101 and of removal of the support layer 2, the bi-adhesive layer 4, 104, in particular the first adhesive surface 6, 106, adheres completely to the surface also after detachment of the silicone layer.

After the step of removal of the silicone support layer, it is possible to proceed with a further step of application, on the second adhesive surface 8 of the bi-adhesive layer attached to the surface 20, of a testing layer having a comparative adhesion surface with a predetermined degree of adhesion. This can be followed by a further step of removal of said testing layer from the bi-adhesive layer 4, 104, following upon which evaluation of the distribution of the fragments of the bi-adhesive layer 4, 104 is carried out. Then the further steps of application and removal of the testing layer and the step of evaluation of the distribution of the fragments can be repeated in sequence for a predetermined number of cycles and with increasing degree of adhesion assigned to the comparative adhesion surface of each testing layer that each time is applied and removed.

This is particularly useful in the case of tests aimed at assessment of the degree of adhesion of a surface and not at mere verification thereof.

Furthermore, it will be appreciated that the fragmented structure of the bi-adhesive layer 4 can comprise fragments of any shape and in general different from that of the quadrangular pieces 10. In addition, it is evident that other production processes may be used that do not envisage the use of cutting blades, for example, laser cutting.

The same principle applies to the layer 104 of the adhesive element 101, where the spheres can be replaced by fragments of a different shape and not spherical.

The invention claimed is:

1. A process for an adhesion test, comprising:
applying an adhesive element to a surface undergoing the adhesion test so as to cause an adhesion between the adhesive element and the surface, wherein the adhesive element includes a bi-adhesive layer with a plurality of fragments and a support layer with a comparative adhesion surface;
removing the support layer from the bi-adhesive layer; and
evaluating a distribution of the fragments of the bi-adhesive layer.

2. The process according to claim 1, wherein evaluating the distribution of the fragments comprises verifying the presence of the fragments on the comparative adhesion surface of the support layer.

3. The process according to claim 1, wherein evaluating the distribution of the fragments comprises verifying the presence of the fragments on the surface.

4. The process according to claim 1, wherein the removal of the support layer from the bi-adhesive layer is executed manually or with automatic means.

5. The process according to claim 1, further comprising a repeated sequence with a predetermined number of cycles of applying a testing layer to the bi-adhesive layer after removing the support layer from the bi-adhesive layer, the testing layer having a comparative adhesion surface with a predetermined degree of adhesion, removing the testing layer from the bi-adhesive layer, evaluating the distribution of the fragments of the bi-adhesive layer, increasing the degree of adhesion of the comparative adhesion surface of the testing layer.

* * * * *